United States Patent [19]

Praefcke et al.

[11] Patent Number: 4,877,220
[45] Date of Patent: Oct. 31, 1989

[54] HEXASUBSTITUTED CYCLOHEXANE COMPOUNDS

[75] Inventors: Klaus Praefcke; Bernd Kohne; Werner Stephan, all of Berlin, Fed. Rep. of Germany

[73] Assignee: Merck Patent Gesellschaft Mit Beschrankter Hafung, Darmstadt, Fed. Rep. of Germany

[21] Appl. No.: 114,365

[22] PCT Filed: Dec. 24, 1986

[86] PCT No.: PCT/EP86/00780
§ 371 Date: Sep. 11, 1987
§ 102(e) Date: Sep. 11, 1987

[87] PCT Pub. No.: WO87/04155
PCT Pub. Date: Jul. 16, 1987

[30] Foreign Application Priority Data

Jan. 11, 1986 [DE] Fed. Rep. of Germany ....... 3600601

[51] Int. Cl.$^4$ .................. C09K 19/30; C09K 19/34; C07C 149/273; C07C 147/02; C07C 147/14; C07D 211/66; C07D 319/06; C07D 339/08
[52] U.S. Cl. ........................... 252/299.61; 252/299.5; 252/299.6; 252/299.62; 252/299.63; 350/350 R
[58] Field of Search ........... 252/299.63, 299.5, 299.61, 252/299.6, 299.62; 350/250 R

[56] References Cited

U.S. PATENT DOCUMENTS

| | | | |
|---|---|---|---|
| 4,333,709 | 6/1982 | Dubois et al. | 252/299.62 |
| 4,578,210 | 3/1986 | Praefcke et al. | 252/299.63 |
| 4,702,562 | 10/1987 | Scheuble et al. | 252/299.63 |
| 4,713,196 | 12/1987 | Praefcke et al. | 252/299.63 |
| 4,734,522 | 3/1988 | Praefcke et al. | 252/299.63 |
| 4,758,373 | 7/1988 | Praefcke et al. | 252/299.63 |

FOREIGN PATENT DOCUMENTS

| | | | |
|---|---|---|---|
| 134576 | 3/1985 | European Pat. Off. | 252/299.63 |
| 1442143 | 7/1976 | United Kingdom | 252/299.63 |

OTHER PUBLICATIONS

Angyal, S. J., et al., J. Chem. Soc., pp. 6949–6955, (1965).
Angyal, S. J., et al., J. Chem. Soc.(C)., pp. 919–992, (1967).
Kok, D. M., et al., Mol. Crystl. Lir. Cryst., vol. 129, pp. 53–60, (1985).
Angyal, S. J., et al., J. Chem. Soc.(C), pp. 919–922, (1967).
C.A., vol. 101:152229y, (1984).
C.A., vol. 76:154058f, (1972).

*Primary Examiner*—Teddy S. Gron
*Attorney, Agent, or Firm*—Millen, White & Zelano

[57] ABSTRACT

Hexasubstituted cyclohexane compounds of the formula I

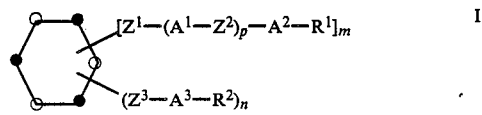

in which $Z^1$, $Z^2$, $Z^3$, $X^1$, $X^2$, $A^1$, $A^2$ and $A^3$, p, $R^1$ and $R^2$, m and (n+m) have the meanings given in claim 1, are suitable as components of discotic liquid-crystalline phases.

5 Claims, No Drawings

HEXASUBSTITUTED CYCLOHEXANE COMPOUNDS

The invention relates to hexasubstituted cyclohexane compounds of the formula I

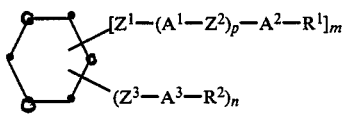

in which $Z^1$ is —CO—$X^1$—, —$X^1$—CO—, —$CH_2$—$X^2$—, —$X^2$—$CH_2$— or —$CH_2$—$CH_2$—, $Z^2$ has one of the meanings of $Z^1$ or is a single bond, $Z^3$ is —$X^1$—CO— or —$X^2$—$CH_2$—

$X^1$ is O, S or Se, $X^2$ is O, S, Se, SO or $SO_2$, $A^1$, $A^2$ and $A^3$ each are, independently of one another, a 1,4-phenylene group which is unsubstituted or mono- or poly-substituted by halogen atoms and/or $CH_3$ groups and/or CN groups and in which one or more CH groups might also be replaced by N atoms, or are a 1,4-cyclohexylene group in which one or two non-adjacent $CH_2$ groups might also be replaced by —O— and/or —S—, or are a piperidine-1,4-diyl group or a 1,4-bicyclo[2.2.2]octylene group, and $A^2$ and $A^3$ can also be a single bond, p is 0 or 1, $R^1$ and $R^2$ each are, independently of one another, alkyl having 1 to 20 C atoms, wherein one or more $CH_2$ groups might also be replaced by —O—, —S—, —$CHCH_3$—, —CHCN—, —CHhalogen—, —CO—, —O—CO—, —CO—O— and/or —CH=CH—, or are H, F, Cl, Br, I, OH, $NH_2$, COOH or CN, no two heteroatoms being directly linked to one another, m is 1, 2 or 3 and (n+m) is 6, with the proviso that, in at least one group, $Z^1$ is other than —$X^1$—CO—.

For simplicity, in the text which follows, "Cy" is a cyclohexane-1,2,3,4,5,6-hexayl group with six free valencies, Cyc is a trans-1,4-cyclohexylene group in which one or two non-adjacent $CH_2$ groups can also be replaced by O and/or S, and Phe is a 1,4-phenylene group in which one or more CH groups can also be replaced by N. The groups Cyc and Phe can be unsubstituted or laterally substituted.

Similar compounds, namely hexaalkanoylcyclohexanes, are known (compare German Offenlegungsschrift No. 3,332,955; B. Kohne and K. Praefcke, Angew. Chem. 96 (1984), 70–71; Z. Luz, W. Poules, R. Poupko, K. Praefcke and B. Scheuble, 21st Bunsen Kolloquium, Berlin Technical University, September/October 1983; German Offenlegungsschrift No. 3,510,325).

The compounds of the formula I can, like similar compounds, be used as components of discotic liquid-crystal-line phases, in particular for displays based on the guest/host effect, the effect of the deformation of aligned phases, the effect of dynamic scattering or on a change in the elliptization of light.

It was the object of the invention to discover novel stable liquid-crystalline or mesogenic compounds which are suitable as components of discotic liquid-crystalline phases. This object has been achieved by the provision of the compounds of the formula I.

It has been found that the compounds of the formula I are outstandingly suitable as components of discotic liquid-crystalline phases. In particular, stable discotic liquid-crystalline phases with a wide mesophase temperature range in a position advantageous for electro-optical effects and very advantageous values of the dielectric anisotropy can be prepared by means of these compounds.

The compounds of the formula I are also suitable as an anisotropic, discotic matrix for spectroscopic investigations.

Other compounds having discotic properties and their use in electro-optical display elements have been described, for example, in U.S. Patent Specification No. 4,333,709. However, the discotic liquid crystals known for this field of application all have a relatively small $\Delta\epsilon$ value for the dielectric anisotropy, since this anisotropy is to be attributed only to the anisotropy of the polarizability of these molecules. Although polar discotic liquid crystals of the phthalocyanine type are already known from C. Piechocki and J. Simon, J. Chem. Soc., Chem. Commun. 1085 (5), 259, the cyclohexane compounds according to the invention by contrast combine the advantages of non-polar cyclohexane compounds, known from German Offenlegungsschriften Nos. 3,332,955 and 3,510,325, with a permanent dipole character.

Surprisingly, the compounds of the formula I prove to be discotic liquid crystalline compounds with, in some cases, very wide meso ranges and particularly advantageous values of the dielectric anisotropy. The compounds of the formula I are discotic liquid crystals with a $\Delta\epsilon$ also based on a permanent dipole character and thus make it possible to provide electro-optical display elements according to U.S. Patent Specification No. 4,333,709 with substantially more advantageous threshold voltages.

Moreover, with the provision of the compounds of the formula I, the range of liquid-crystalline substances, which are suitable for the preparation of liquid-crystalline mixtures under various application aspects, is quite generally broadened considerably.

The compounds of the formula I are also suitable as intermediates for the preparation of other substances which can be used as constituents of liquid-crystalline discotic phases.

In the pure state, the compounds of the formula I are colorless and form liquid-crystalline mesophases in a temperature range suitable for electro-optical use. They are very stable chemically, thermally and towards light.

The invention thus relates to the compounds of the formula I. The invention also relates to the use of the compounds of the formula I as components of discotic liquid-crystalline phases.

In addition, the invention relates to discotic liquid-crystalline phases with a content of at least one compounds (sic) of the formula I and to liquid crystal display elements which contain such phases.

Furthermore, the invention relates to an electro-optical display element which contains a discotic liquid-crystalline material which can be electrically switched between two different optical states and is enclosed between two electrode base plates each with one electrically conductive electrode layer.

Above and below, $Z^1$, $Z^2$, $Z^3$, $X^1$, $X^2$, $A^1$, $A^2$, $A^3$, p, $R^1$, $R^2$, m and n are as defined above, unless explicitly stated otherwise.

Accordingly, the compounds of the formula I comprise those of the part formulae Ia, Ib and Ic:

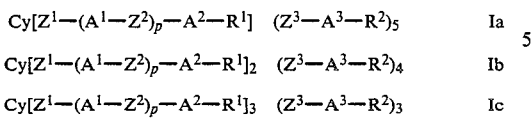

Those compounds of the formula Ia and also those of the part formula Ib and Ic are preferred in which the substituents $Z^1$—$(A^1$—$Z^2)_p$—$A^2$—$R^1$, which appear only twice or three times, are identical and are located, respectively, in the 1,4- or 1,3,5-positions of the cyclohexane system.

Particularly preferred meanings of —$(A^1$—$Z^2)_p$—$A^2$— are:

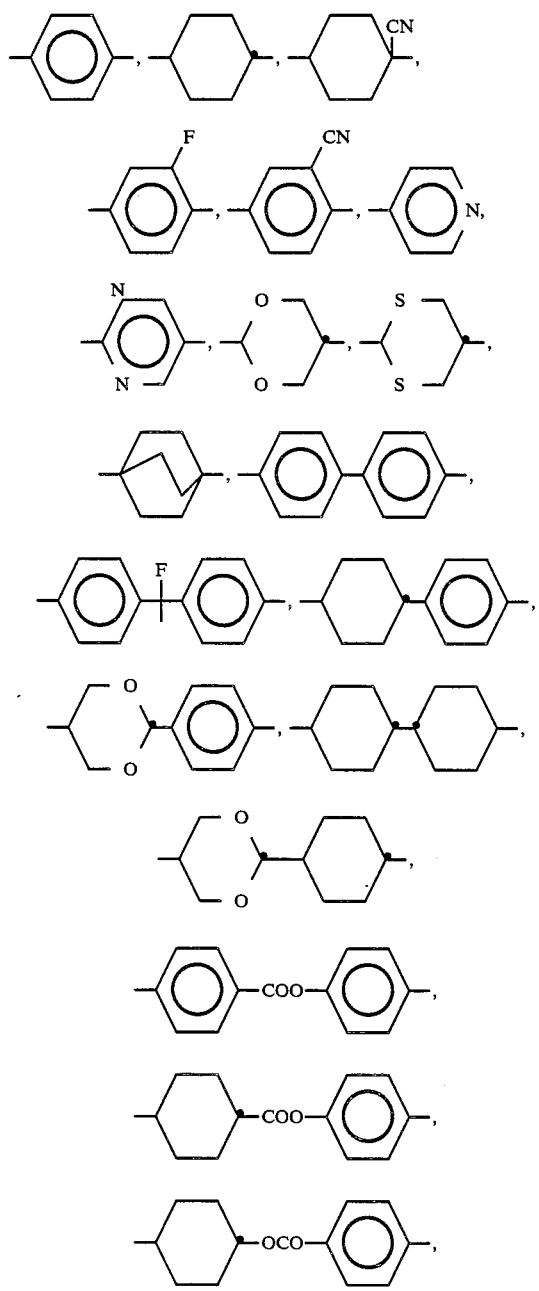

-continued

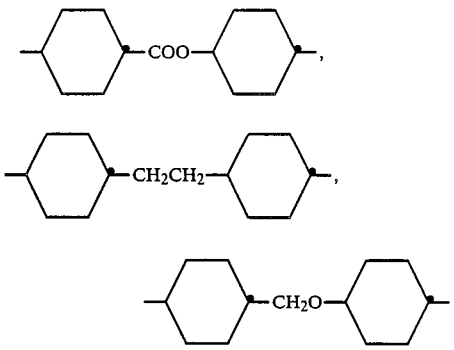

Moreover, amongst the cyclohexanes of the formula I, those are preferred in which the substituents opposite one another are in each case equatorial and in the trans-position relative to one another. This corresponds to the configuration of scyllo-inositol.

Compounds of the formula I which have one or more asymmetric C atoms can be in the racemic or in the optically active form, both forms being covered by formula I.

$R^1$ and/or $R^2$ are preferably an alkyl radical in which one or two $CH_2$ groups can also be replaced by O atoms (oxaalkyl or dioxaalkyl respectively). These radicals can be straight-chain or branched. Preferably, they are straight-chain and have 3, 4, 5, 6, 7, 8, 9, 10, 11, 12 or 13 C atoms and accordingly are preferably propyl, butyl, pentyl, hexyl, heptyl, octyl, nonyl, decyl, undecyl, dodecyl, tridecyl, 2-oxapropyl (=methoxymethyl), 2-oxabutyl (=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, and also ethyl, tetradecyl, pentadecyl, 2-, 3-, 4-, 5-, 6- or 7-oxaoctyl, 2-, 3-, 4-, 5-, 6-, 7- or 8-oxanonyl, 2-, 3-, 4-, 5-, 6-, 7-, 8- or 9-oxadecyl, 2-, 3-, 4-, 5-, 6-, 7-, 8-, 9- or 10-oxaundecyl, 2-, 3-, 4-, 5-, 6-, 7-, 8-, 9-, 10- or 11-oxadodecyl, 2-, 3-, 4-, 5-, 6-, 7-, 8-, 9-, 10-, 11- or 12-oxatridecyl, 2,4-dioxapentyl, 2,4-, 2,5- or 3,5-dioxahexyl or 2,4-, 2,5-, 2,6-, 3,5-, 3,6- or 4,6-dioxaheptyl.

Compounds of the formulae I with branched groups R may sometimes be of importance because of higher solubility in the usual liquid-crystalline base materials, but especially as chiral doping substances, if they are optically active. Branched groups of this type as a rule do not contain more than one chain branching. Preferred branched radicals R contain one * —$CHCH_3$-, * —CHCN— or * —CH— halogen group and are preferably 2-butyl (=1-methylpropyl), isobutyl (=2-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, 2-octyl, isopropoxy, 2-methylpropoxy, 2-methylbutoxy, 3-methylbutoxy, 2-methylpentoxy, 3-methylpentoxy, 2-ethylhexoxy, 1-methylhexoxy, 1-methylheptoxy, 2-oxa-3-methylbutyl, 3-oxa-4-methylpentyl, 2-octyloxy, 2-chloropropionyloxy, 2-chloro-3-methylbutyryloxy, 2-chloro-4-methylvaleryloxy, 2-chloro-3-methylvaleryloxy, 2-methyl-3-oxapentyl and 2-methyl-3-oxahexyl.

$Z^1$ is preferably —$X^1$—CO— or —$X^2$—$CH_2$. $Z^2$ is preferably —O—CO—, —CO—O— or a single bond. $Z^3$ is preferably —O—CO—. $X^1$ is preferably O or S, and especially preferably O. $X^2$ is preferably O, S, SO or $SO_2$, especially preferably S or $SO_2$.

$A^1$, $A^2$ and $A^3$ preferably each are, independently of one another, 1,4-phenylene or trans-1,4-cyclohexylene. $A^2$ and $A^3$ as single bonds are also preferred.

$R^1$ and $R^2$ are preferably alkyl groups having preferably 3 to 13 C atoms. If $R^1$ and $R^2$ are directly linked to a group $A^1$, $A^2$ or $A^3$ other than a single bond, $R^1$ and $R^2$ can preferably also be alkoxy or oxaalkyl having preferably 2 to 12 C atoms, alkenyl having 3 to 13 C atoms, H, F, Cl, Br, I, OH, $NH_2$, COOH or CN.

If $R^1$ or $R^2$ is directly linked to a trans-1,4-cyclohexylene group, these groups are preferably alkyl. If $R^1$ or $R^2$ is directly linked to a 1,4-phenylene group, these groups are preferably alkyl, alkoxy or H, F, Cl, Br, I, OH, $NH_2$, COOH or CN.

In the case of p=1 and $A^2$=a single bond, $Z^2$ is preferably a single bond.

m is preferably 1. n is preferably 5.

Amongst the compounds of the formulae I and Ia to Ic, those are preferred in which at least one of the possible radicals has one of the preferred meanings indicated.

The compounds of the formula I are prepared by methods known per se, such as are described in the literature (for example in the standard works such as Houben-Weyl, Methoden der Organischen Chemie [Methods of Organic Chemistry], Georg-Thieme-Verlag, Stuttgart), and especially under reaction conditions which are known and suitable for the reactions mentioned. Variants which are known per se but not mentioned here specifically can also be used.

The starting materials are either known or can be prepared to known compounds. If desired, they can also be formed in situ, in such a way that they are not isolated from the reaction mixture but immediately converted further to the compounds of the formula I.

Ethers of the formula I (wherein at least one of the groups $Z^1$, $Z^2$ and $Z^3$ is —O—$CH_2$— or —$CH_2$—O—) are obtainable by etherification of corresponding hydroxy compounds, the hydroxy compound preferably being first converted into a corresponding metal derivative, for example into the corresponding alkali metal alcoholate or alkali metal phenolate by treatment with NaH, $NaNH_2$, NaOH, KOH, $Na_2CO_3$ or $K_2CO_3$. This alcoholate or phenolate can then be reacted with the appropriate alkyl halide, sulfonate or dialkyl sulfate, preferably in an inert solvent such as acetone, 1,2-dimethoxyethane, dimethylformamide (DMF) or dimethyl sulfoxide, or also in an excess of aqueous or aqueous-alcoholic NaOH or KOH at temperatures between about 20° and 100°.

Esters of the formula I wherein, for example, at least one of the groups $Z^1$, $Z^2$ and $Z^3$ is —O—CO— or —CO—O— are obtainable by esterification of corresponding carboxylic acids. In place of the carboxylic acids and/or the alcohols, reactive derivatives thereof can also be used.

Suitable reactive derivatives of the said carboxylic acids are especially the acid halides, above all the chlorides and bromides, and also the anhydrides, for example also mixed anhydrides, azides or esters, especially alkyl esters having 1-4 C atoms in the alkyl group. Reactive derivatives of the said alcohols can especially be the corresponding metal alcoholates, where OH group(s) take(s) the place of the OH group(s) and M is one equivalent of a metal, preferably an alkali metal such as Na or K.

The esterification is advantageously carried out in the presence of an inert solvent. Especially ethers such as diethyl ether, di-n-butyl ether, THF, dioxane or anisole, ketones such as acetone, butanone or cyclohexanone, amides such as DMF or phosphoric acid hexamethyltriamide, hydrocarbons such as benzene, toluene or xylene, halogenohydrocarbons such as carbon tetrachloride or tetrachloroethylene, sulfoxides such as dimethyl sulfoxide or sulfolan and carboxylic acids such as trifluoroacetic acid are very suitable. Water-immiscible solvents can at the same time be used advantageously for azeotropically distilling off the water formed in the esterification. Occasionally, an excess of an organic base, for example pyridine, quinoline or triethylamine, can also be used as the solvent for the esterification. The esterification can also be carried out in the absence of a solvent, for example by simple heating of the components in the presence of sodium acetate. The reaction temperature is usually between $-50°$ and $+250°$, preferably between $-20°$ and $+80°$. At these temperatures, the esterification reactions are as a rule complete after 15 minutes to 48 hours.

In detail, the reaction conditions for the esterification depend largely on the nature of the starting materials used. Thus, a free carboxylic acid is reacted with a free alcohol as a rule in the presence of a strong acid, for example a mineral acid such as hydrochloric acid or sulfuric acid. A preferred reaction procedure is the reaction of an acid anhydride or especially an acid chloride with an alcohol, preferably in a basic medium, especially alkali metal hydroxides such as sodium or potassium hydroxide, alkali metal carbonates or hydrogen carbonates such as sodium carbonate, sodium hydrogen carbonate, potassium carbonate or potassium hydrogen carbonate, alkali metal acetates, such as sodium or potassium acetate, alkaline earth metal hydroxides such as calcium hydroxide or organic bases such as triethylamine, pyridine, lutidine, collidine or quinoline being of importance as bases. A further preferred embodiment of the esterification comprises converting the alcohol first into the sodium or potassium alcoholate, for example by treatment with ethanolic sodium or potassium hydroxide solution, isolating the alcoholate and suspending it together with sodium hydrogen carbonate or potassium carbonate in acetone or diethyl ether with stirring and adding to this suspension a solution of the acid chloride or anhydride in diethyl ether, acetone or DMF, preferably at temperatures between about $-25°$ and $+20°$.

Thioethers of the formula I, wherein at least one of the groups $Z^1$, $Z^2$ and $Z^3$ is —S—$CH_2$— or —$CH_2$—S—, can be prepared by reacting a corresponding halogen compound or a corresponding sulfonate, preferably the corresponding mesylate, with a corresponding thiol or—preferably—one of its salts, in particular the corresponding Na thiolate. This reaction can be carried out in the presence or absence of an inert solvent, in particular at temperatures between about $-20°$ and $250°$, preferably between $10°$ and $150°$ C. Examples of suitable solvents are hydrocarbons such as benzene, toluene, xylenes or mesitylene, tertiary bases such as triethylamine, pyridine or picolines, alcohols such as methanol, ethanol or butanol, glycols and glycol ethers such as ethylene glycol, diethylene glycol and 2-methoxyethanol, ketones such as acetone, ethers such as tetrahydrofuran or dioxane, amides such as DMF or phosphoric acid hexamethyltriamide (HMPT) or sulfoxides such as dimethyl sulfoxide. Mixtures of these solvents are also suitable.

Sulfoxides and sulfones of the formula I can be prepared by oxidation of corresponding thioethers of the formula I.

Depending on the chosen reagent and the conditions applied, the thioethers are oxidized to the corresponding sulfoxides or to the corresponding sulfones, methods known per se from the literature being used, and the detailed reaction conditions being easily found in the literature. If the sulfoxides are to be obtained, the oxidation is carried out, for example, with hydrogen peroxide, peracids, Cr(VI) compounds such as chromic acid, nitric acid, nitrous gases, $N_2O_3$, halogen such as chlorine, hypochlorites, periodate, $KMnO_4$, N-bromosuccinimide, 1-chlorobenzotriazole, Ce(IV) compounds such as $(NH_4)_2Ce(NO_3)_6$, negatively substituted aromatic diazonium salts such as o- or p-nitrophenyldiazonium chloride or electrolytically under relatively mild conditions and at relatively low temperatures (about $-80°$ to $+100°$). If, however, it is intended to obtain the sulfones, the same oxidizing agents are used under more severe conditions and/or in an excess, and as a rule at higher temperatures. In these reactions, the usual inert solvents can be present or absent. Examples of suitable solvents are water, aqueous mineral acids, aqueous alkali metal hydroxide solutions, lower alcohols such as methanol or ethanol, esters such as ethyl acetate, ketones such as acetone, lower carboxylic acids such as acetic acid, nitriles, such as acetonitrile, hydrocarbons such as benzene or chlorinated hydrocarbons such as chloroform or $CCl_4$.

A preferred oxidizing agent is 30% aqueous hydrogen peroxide. When the calculated amount is used in solvents such as acetic acid, acetone, ethanol or aqueous sodium hydroxide solution at temperatures between $-20°$ and $100°$, this leads to the sulfoxides, and an excess at higher temperatures, preferably in acetic acid or in a mixture of acetic acid and acetic anhydride, leads to the sulfones.

A further preferred oxidizing agent is 3-chloroperbenzoic acid. In general, this leads to the sulfones in solvents such as halogenohydrocarbons at temperatures between 0° and 65°. . . . (sic) the corresponding sulfoxides are sometimes also formed.

A further possible way to prepare the sulfoxides is to treat the thioethers with chlorine, for example in moist benzene or in acetic acid. The dichloro compounds obtained as intermediates are very readily converted by hydrolysis into the sulfoxides.

The discotic liquid-crystalline phases according to the invention consist of 2 to 15, preferably 3 to 12, components, including at least one compound of the formula I. The other constituents are preferably selected from the known discotic liquid-crystalline substances, in particular from the classes of hexasubstituted benzene or triphenylene derivatives. The phases according to the invention contain about 0.1 to 100%, preferably 10 to 100%, of one or more compounds of the formula I.

The discotic liquid-crystalline phases according to the invention are prepared in the manner conventional per se. As a rule, the components are dissolved in one another, preferably at an elevated temperature.

The discotic liquid-crystalline phases according to the invention can also be modified by suitable additives. For example, it is possible to add conductive salts for improving the conductivity, pleochoic (sic) dyes or substances for modifying the dielectric anisotropy, the viscosity and/or the orientation of the discotic phases.

The examples which follow are intended to illustrate the invention without limiting it. F=melting point, C=clear point. Above and below, percentage data mean percent by weight; all temperatures are stated in degrees Celcius (sic). "Usual working up" means: addition of water, extraction with methylene chloride, separation, crying of the organic phase, evaporation and purification of the product by crystallization and/or chromatography.

EXAMPLE 1

6 ml of freshly distilled benzylmercaptan are added slowly at 0° C. with stirring to a mixture of 1.5 g of sodium hydride (80% suspension in oil) in 50 ml of absolute dimethylformamide and the mixture is stirred for 2 hours under nitrogen at room temperature. 2.34 g (5 mmol) of 1,3,4,5,6-penta-O-acetyl-2-O-mesyl-myo-inositol are then added and the mixture is stirred for 16 hours at 50° C. while excluding air. The batch is poured onto ice, acidified with 2N HCl and extracted with three times 50 ml of $CHCl_3$. The aqueous phase is evaporated to dryness, and the residue is dried in a high vacuum (about 0.1 mm Hg) and heated for 1 hour with stirring to 100° C. with a mixture of 35 ml of pyridine and 30 ml of acetic anhydride. The mixture is poured onto ice, acidified with concentrated HCl and extracted with three times 25 ml of ethyl acetate. The combined organic extracts were shaken with $H_2O$, three times with saturated $NaHCO_3$ solution and saturated NaCl solution and dried over magnesium sulfate. After evaporation of the solvent, a crystalline solid remains which is recrystallized from ethanol (F. 168°–170° C.). For further purification, the product obtained is chromatographed through a column (silica gel/$CHCl_3$) and recrystallized from ethanol. This gives 2,3,4,5,6-penta-O-acetyl-1S-benzylthio-1-deoxy-scylloinositol, F. 185°–187°.

$^1$H-NMR (400 MHz, $CDCl_3$): $\delta=7.32$–7.21 (m, 5H aromatic), 5.23–5.12 (m, 5H aliphatic ring), 3.77 (s, 2H, —S—$CH_2$—), 2.73 (dd, 1H, C aliphatic ring, J=11+11 Hz), 2.07 (s, 6H, —$CH_3$), 2.01 (s, 6H, —$CH_3$), 1.99 (s, 3H, —$CH_3$).

MS 210° C.: m/e (%)=496 ($M^+$-$CH_3CO$, 0.1), 437 ($M^+$-$CH_3CO_2$, 0.1), 405 ($M^+$-$C_6H_5$—$CH_2$), 0.04), 376 ($M^+$-2$CH_3$—COOH), 18), 316 ($M^+$-3$CH_3$—COOH), 21), 274 (19), 232 (26), 183 (5), 152 (6), 141 (5), 123 ($M^+$-$C_6H_5CH_2$-S, 10), 122 (21), 110 (6), 91 ($C_6H_5$—$CH_2$, 100).

The following are prepared analogously:
2,3,4,5,6-penta-O-propionyl-1-S-benzylthio-1-deoxyscyllo-inositol,
2,3,4,5,6-penta-O-butyryl-1-S-benzylthio-1-deoxyscyllo-inositol,
2,3,4,5,6-penta-O-isobutyryl-1-S-benzylthio-1-deoxyscyllo-inositol,
2,3,4,5,6-penta-O-valeryl-1-S-benzylthio-deoxyscyllo-inositol,
2,3,4,5,6-penta-O-capronyl-1-S-benzylthio-1-deoxyscyllo-inositol, F. 45.5°, C. 157.8°
2,3,4,5,6-penta-O-heptanoyl-1-S-benzylthio-1-deoxyscyllo-inositol,
2,3,4,5,6-penta-O-octanoyl-1-S-benzylthio-1-deoxyscyllo-inositol,
2,3,4,5,6-penta-O-nonanoyl-1-S-benzylthio-1-deoxyscyllo-inositol,
2,3,4,5,6-penta-O-decanoyl-1-S-benzylthio-1-deoxyscyllo-inositol, 2,3,4,5,6-penta-O-undecanoyl-1-S-benzylthio-1-deoxys-cyllo-inositol, 2,3,4,5,6-penta-O-dodecanoyl-1-S-benzylthio-1-deoxys-cyllo-inositol,

EXAMPLE 2

A mixture of 2.34 g (5 mmol) of 1,3,4,5,6-penta-O-acetyl-2-O-mesyl-myo-inositol and sodium benzylmercaptide (from 1.5 g of NaH and 6 ml of benzylmercaptan in 50 ml of DMF) is reacted as in Example 1 and worked up in the same way. 5 g (37 mmol) of hexanoyl chloride and 20 ml of trifluoroacetic acid are added to the crude product dried in high vacuum and the mixture is heated with stirring for 15 hours and (sic) 70° C. After the solvent has been distilled off, the residue is taken up in about 70 ml of ethyl acetate. The mixture is extracted with water, washed with saturated $NaHCO_3$ solution until neutral, shaken with saturated NaCl solution and dried over magnesium sulfate. The residue remaining after the solvent has been distilled off is chromatographed on silica gel with 15:1 petroleum ether (30°-70° C.)/ethyl acetate as solvent, and the product thus obtained is recrystallized from ethanol.

This gives 2,3,4,5,6-penta-O-hexanoyl-1S-benzylthio-1-deoxy-scyllo-inositol, F. 45.5°, C. 157.8°, $\mu=2.18$ D (in benzene).

IR ($CHCl_3$): 2960 (CH), 2940 (CH), 1755 (CO), 1155 $cm^{-1}$ $^1$H-NMR (400 MHz, $CDCl_3$): $\delta=7.31-7.19$ (m, 5H aromatic), 5.28–5.18 (m, 5H aliphatic ring), 3.78 (s, 2H, $-CH_2-S-$), 2.73 (dd, J=10+10 Hz, 1H aliphatic ring), 2.37–2.16 (m, 10H, $CH_2$ chain), 1.66–1.46 (m, 10H, $CH_2$ ring), 1.36–1.18 (m, 20H, $CH_2$ ring), 0.91–0.85, 15H, $CH_3$, m).

MS (250° C.): m/e (%)=678 ($M^+$-$C_5H_{11}CO$, 0.04), 676 (0.1), 622 ($M^+$-$C_5H_{11}CO_2$, 0.1), 661 (0.3), 660 (0.2), 544 (0.3), 455 (1.3), 428 (8), 330 (21), 232 (31), 123 ($C_6H_5-CH_2-S^+$, 7), 99 ($C_5H_{11}CO^+$), 100), 91 ($C_6H_5-CH_2^+$, 52).

The following are prepared analogously:

2,3,4,5,6-penta-O-acetyl-1S-benzylthio-1-deoxy-scyllo-inositol, 2,3,4,5,6-penta-O-propionyl-1S-benzylthio-1-deoxy-scyllo-inositol, 2,3,4,5,6-penta-O-butyryl-1S-benzylthio-1-deoxy-scyllo-inositol, 2,3,4,5,6-penta-O-valeryl-1S-benzylthio-1-deoxy-scyllo-inositol, 2,3,4,5,6-penta-O-heptanoyl-1S-benzylthio-1-deoxy-scyllo-inositol, 2,3,4,5,6-penta-O-octanoyl-1S-benzylthio-1-deoxy-scyllo-inositol, 2,3,4,5,6-penta-O-nonanoyl-1S-benzylthio-1-deoxy-scyllo-inositol, 2,3,4,5,6-penta-O-decanoyl-1S-benzylthio-1-deoxy-scyllo-inositol, 2,3,4,5,6-penta-O-undecanoyl-1S-benzylthio-1-deoxy-scyllo-inositol, 2,3,4,5,6-penta-O-dodecanoyl-1S-benzylthio-1-deoxy-scyllo-inositol, 2,3,4,5,6-penta-O-acetyl-1S-4-cyanobenzylthio-1-deoxy-scyllo-inositol, 2,3,4,5,6-penta-O-propionyl-1S-4-cyanobenzylthio-1-deoxy-scyllo-inositol, 2,3,4,5,6-penta-O-butyryl-1S-4-cyanobenzylthio-1-deoxy-scyllo-inositol, 2,3,4,5,6-penta-O-valeryl-1S-4-cyanobenzylthio-1-deoxy-scyllo-inositol, 2,3,4,5,6-penta-O-heptanoyl-1S-4-cyanobenzylthio-1-deoxy-scyllo-inositol, 2,3,4,5,6-penta-O-octanoyl-1S-4-cyanobenzylthio-1-deoxy-scyllo-inositol, 2,3,4,5,6-penta-O-nonanoyl-1S-4-cyanobenzylthio-1-deoxy-scyllo-inositol, 2,3,4,5,6-penta-O-decanoyl-1S-4-cyanobenzylthio-1-deoxy-scyllo-inositol, 2,3,4,5,6-penta-O-undecanoyl-1S-4-cyanobenzylthio-1-deoxy-scyllo-inositol, 2,3,4,5,6-penta-O-dodecanoyl-1S-4-cyanobenzylthio-1-deoxy-scyllo-inositol,

EXAMPLE 3

A mixture of 590 mg (0.76 mmol) of 2,3,4,5,6-penta-O-hexanoyl-1-S-benzylthio-1-deoxy-scyllo-inositol, 262 mg (1.5 mmol) of m-chloroperbenzoic acid and 30 ml of chloroform is boiled for 17 hours under reflux. After cooling, the mixture is extracted with four times 30 ml of saturated $NaHCO_3$ solution, and the organic phase is separated off and dried over $MgSO_4$. After the solvent has been distilled off, the residue is purified by column chromatography on silica gel with 10:1 petroleum ether (30°-70° C.)/ethyl acetate as solvent and the product thus obtained is recrystallized from ethanol.

This gives 2,3,4,5,6-penta-O-hexanoyl-1S-benzylsulfono-1-deoxy-scyllo-inositol, F. 95.5°, C. 188.9° (decomposition), $\mu=3.49$ D (in benzene).

| | calculated | found |
|---|---|---|
| $C_{43}H_{68}O_{12}S$ | C 63.83 | C 63.94 |
| 809.03 | H 8.47 | H 8.18 |

IR ($CHCl_3$): 2960 (CH), 2930 (CH), 1755 (CO), 1335 ($SO_2$), 1160 ($SO_2$)

$^1$H-NMR (400 MHz, $CDCl_3$) $\delta=7.43-7.38$, 7.38–7.32, (m, 5H aromatic), 5.59 (d, 1H, aliphatic ring), J=10 Hz), 5.56 (d, 1H, aliphatic ring, J=10 Hz), 5.27–5.16 (m, 3H, aliphatic ring), 4.37 (s, 2H, $-SO_2CH_2-$), 3.49 (dd, J=10+10 Hz, 1H aliphatic ring), 2.30–2.14 (m, 10H $-CH_2$ chain), 1.62–1.48 (m, 10H, $CH_2$ chain), 1.36–1.18 (m, 20H, $CH_2$ chain), 0.93–0.88 (m, 15H, $CH_3$)

MS (200° C.): m/e (%)=808 ($M^+$-1, 0.05), 807 (0.08), 752 (0.1), 710 (0.1), 694 ($M^+$-$C_5H_{11}CO_2$, 0.1), 693 (0.4), 692 (1), 691 (1), 579 ($M^+$-2$C_5H_{11}CO_2$, 0.2), 99 ($C_5H_{11}CO^+$, 100), 91 ($C_6H_5-CH_2^+$, 83).

The following are prepared analogously:

2,3,4,5,6-penta-O-acetyl-1S-benzylsulfono-1-deoxy-scyllo-inositol, 2,3,4,5,6-penta-O-propionyl-1S-benzylsulfono-1-deoxy-scyllo-inositol, 2,3,4,5,6-penta-O-butyryl-1S-benzylsulfono-1-deoxy-scyllo-inositol, 2,3,4,5,6-penta-O-valeryl-1S-benzylsulfono-1-deoxy-scyllo-inositol, 2,3,4,5,6-penta-O-heptanoyl-1S-benzylsulfono-1-deoxy-scyllo-inositol, 2,3,4,5,6-penta-O-octanoyl-1S-benzylsulfono-1-deoxy-scyllo-inositol, 2,3,4,5,6-penta-O-nonanoyl-1S-benzylsulfono-1-deoxy-scyllo-inositol, 2,3,4,5,6-penta-O-decanoyl-1S-benzylsulfono-1-deoxy-scyllo-inositol, 2,3,4,5,6-penta-O-undecanoyl-1S-benzylsulfono-1-deoxy-scyllo-inositol, 2,3,4,5,6-penta-O-dodecanoyl-1S-benzylsulfono-1-deoxy-scyllo-inositol, 2,3,4,5,6-penta-O-acetyl-1S-4-cyanobenzylsulfono-1-deoxy-scyllo-inositol,
2,3,4,5,6-penta-O-propionyl-1S-4-cyanobenzylsulfono-1-deoxy-scyllo-inositol,
2,3,4,5,6-penta-O-butyryl-1S-4-cyanobenzylsulfono-1-deoxy-scyllo-inositol,
2,3,4,5,6-penta-O-valeryl-1S-4-cyanobenzylsulfono-1-deoxy-scyllo-inositol,
2,3,4,5,6-penta-O-heptanoyl-1S-4-cyanobenzylsulfono-1-deoxy-scyllo-inositol,
2,3,4,5,6-penta-O-octanoyl-1S-4-cyanobenzylsulfono-1-deoxy-scyllo-inositol,
2,3,4,5,6-penta-O-nonanoyl-1S-4-cyanobenzylsulfono-1-deoxy-scyllo-inositol,
2,3,4,5,6-penta-O-decanoyl-1S-4-cyanobenzylsulfono-1-deoxy-scyllo-inositol,
2,3,4,5,6-penta-O-undecanoyl-1S-4-cyanobenzylsulfono-1-deoxy-scyllo-inositol,
2,3,4,5,6-penta-O-dodecanoyl-1S-4-cyanobenzylsulfono-1-deoxy-scyllo-inositol,

EXAMPLE 4

A mixture of 2-O-mesyl-1,3,4,5,6-penta-O-benzyl-myo-inositol (obtainable from known 1,3,4,5,6-penta-O-benzyl-myo-inositol by reaction with methanesulfonyl chloride in pyridine) and excess sodium salt of phenylmethanethiol in DMF is stirred for 48 hours at 80°. After usual working-up, this gives S-benzyl-penta-O-benzyl-scyllo-monothioinositol, F. 149.5°–150°.

The following are obtained analogously:
S-benzyl-penta-O-benzyl-scyllo-monoselenoinositol, F. 131°–134°
S-(p-cyanobenzyl)-penta-O-(p-methylbenzyl)-scyllo-monothioinositol,
S-(p-cyanobenzyl)-penta-O-(p-ethylbenzyl)-scyllo-monothioinositol,
S-(p-cyanobenzyl)-penta-O-(p-propylbenzyl)-scyllo-monothioinositol,
S-(p-cyanobenzyl)-penta-O-(p-butylbenzyl)-scyllo-monothioinositol,
S-(p-cyanobenzyl)-penta-O-(p-pentylbenzyl)-scyllo-monothioinositol,
S-(p-cyanobenzyl)-penta-O-(p-hexylbenzyl)-scyllo-monothioinositol,
s-(p-cyanobenzyl)-penta-O-(p-heptylbenzyl)-scyllo-monothioinositol,
S-(p-cyanobenzyl)-penta-O-(p-octylbenzyl)-scyllo-monothioinositol,
S-(p-cyanobenzyl)-penta-O-(p-nonylbenzyl)-scyllo-monothioinositol,
S-(p-cyanobenzyl)-penta-O-(p-decylbenzyl)-scyllo-monothioinositol,
s-(p-cyanobenzyl)-penta-O-(p-butoxybenzyl)-scyllo-monothioinositol,
S-(p-cyanobenzyl)-penta-O-(p-pentoxybenzyl)-scyllo-monothioinositol,
S-(p-cyanobenzyl)-penta-O-(p-hexoxybenzyl)-scyllo-monothioinositol,
S-(p-cyanobenzyl)-penta-O-(p-heptoxybenzyl)-scyllo-monothioinositol,
S-(p-cyanobenzyl)-penta-O-(p-octoxybenzyl)-scyllo-monothioinositol,
S-(p-cyanobenzyl)-penta-O-(p-nonoxybenzyl)-scyllo-monothioinositol,
S-(p-cyanobenzyl)-penta-O-(p-decoxybenzyl)-scyllo-monothioinositol,
S-n-hexyl-penta-O-benzyl-scyllo-monothioinositol, F. 79°–81°, C. 68.9°,
S-hexyl-penta-O-(p-methylbenzyl)-scyllo-monothioinositol,
S-hexyl-penta-O-(p-ethylbenzyl)-scyllo-monothioinositol,
S-hexyl-penta-O-(p-propylbenzyl)-scyllo-monothioinositol,
S-hexyl-penta-O-(p-butylbenzyl)-scyllo-monothioinositol,
S-hexyl-penta-O-(p-pentylbenzyl)-scyllo-monothioinositol,
S-hexyl-penta-O-(p-hexylbenzyl)-scyllo-monothioinositol,
S-hexyl-penta-O-(p-heptylbenzyl)-scyllo-monothioinositol,
S-hexyl-penta-O-(p-octylbenzyl)-scyllo-monothioinositol,
S-hexyl-penta-O-(p-nonylbenzyl)-scyllo-monothioinositol,
S-hexyl-penta-O-(p-decylbenzyl)-scyllo-monothioinositol,
S-hexyl-penta-O-(p-butoxybenzyl)-scyllo-monothioinositol,
S-hexyl-penta-O-(p-pentoxybenzyl)-scyllo-monothioinositol,
S-hexyl-penta-O-(p-hexoxybenzyl)-scyllo-monothioinositol,
S-hexyl-penta-O-(p-heptoxybenzyl)-scyllo-monothioinositol,
S-hexyl-penta-O-(p-octoxybenzyl)-scyllo-monothioinositol,
S-hexyl-penta-O-(p-nonoxybenzyl)-scyllo-monothioinositol,
S-hexyl-penta-O-(p-decoxybenzyl)-scyllo-monothioinositol.

We claim:

1. A discotic liquid-crystalline phase comprising at least two liquid-crystalline components, wherein at least one component is a been substituted therefor hexasubstituted cyclohexane compound of the formula I $$[Z^1-(A^1-Z^2)_p-A^2-R^1]_m \quad\quad I$$
$$(Z^3-A^3-R^2)_n$$

wherein $Z^1-(A^1-Z^2)_p-A^2-R^1$ is different from $Z^3-A^3R^2$ and
in which
$Z^1$ is $-CO-X^1-$, $-X^1-CO-$, $-CH_2-X^2-$, $-X^2-CH_2-$ or $-CH_2-CH_2-$,
$Z^2$ has one of the meanings of $Z^1$ or is a single bond,
$Z^3$ is $-X^1-CO-$ or $-X^2-CH_2-$
$X^1$ is O, S or Se,
$X^2$ is O, S, Se, SO or $SO_2$,
$A^1$, $A^2$ and $A^3$ each are, independently of one another, a 1,4-phenylene group which is unsubstituted or mono- or poly-substituted by halogen atoms and/or $CH_3$ groups and/or CN groups and in which one or more CH groups might also be replaced by N atoms, or are a 1,4-cyclohexylene group in which one or two non-adjacent $CH_2$ groups might also be replaced by $-O-$ and/or $-S-$, or are a piperidine-1,4-diyl group or a 1,4-bicyclo[2.2.2]octylene group, and $A^2$ and $A^3$ can also be a single bond,
p is [0 or] 1, $R^1$ and $R^2$ each are, independently of one another, alkyl having 1 to 20 C atoms, wherein one or more $CH_2$ groups might also be replaced by —O—, —S—, —CHCH$_3$, —CHCN—, —CHhalogen—, —CO—, —O—CO—, —CO—O— and/or —CH=CH—, or are H, F, Cl, Br, I, OH, $NH_2$, COOH or CN, no two heteroatoms being directly linked to one another, m is 1, 2 or 3 and (n+m) is 6, with the proviso that, in at least one group, $Z^1$ is other than —$X^1$—CO—.

2. A liquid crystal display element comprising a liquid-crystalline phase, wherein said phase is one of claim 1.

3. A discotic liquid-crystalline phase of claim 1 comprising a hexasubstituted cyclohexane compound of formula I in which $A^1$ is 1,4-phenylene, 1,4-phenylene which is substituted by CN or halogen, 1,4-cyclohexylene, pyrimidin-2,5-diyl, dioxane-2,5-diyl or dithiane-2,5-diyl.

4. A discotic liquid-crystalline phase of claim 1 comprising a hexasubstituted cyclohexane compound of formula I in which $A^2$ and $A^3$ each are, independently of one another, 1,4-phenylene, 1,4-cyclohexylene or a single bond.

5. A discotic liquid-crystalline phase of claim 1 comprising a hexasubstituted cyclohexane compound of formula I in which $Z^1$ is $X^1$—CO or $X^2$—$CH_2$, $Z^2$ is O—CO, CO—O or a single bond and $Z^3$ is O—CO or O—$CH_2$.

* * * * *

UNITED STATES PATENT AND TRADEMARK OFFICE
CERTIFICATE OF CORRECTION

PATENT NO. : 4,877,220

DATED : October 31, 1989

INVENTOR(S) : KLAUS PRAEFCKE ET AL

It is certified that error appears in the above-identified patent and that said Letters Patent is hereby corrected as shown below:

Column 12, claim 1, line 39:

reads "least one component is a been substituted therefor hex-"

should read -- least one component is a hex- --

Signed and Sealed this

Twenty-seventh Day of November, 1990

Attest:

HARRY F. MANBECK, JR.

*Attesting Officer*      *Commissioner of Patents and Trademarks*